United States Patent
Tanaka et al.

[11] Patent Number: 6,096,557
[45] Date of Patent: *Aug. 1, 2000

[54] GAS DETECTION METHOD AND APPARATUS USING GAS REACTIVE PIGMENT

[75] Inventors: Kazunari Tanaka; Chiaki Igarashi, both of Kanagawa-ken; Yoshihiko Sadaoka, Ehime-ken, all of Japan

[73] Assignee: Ebara Corporation, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/910,231

[22] Filed: Aug. 13, 1997

[30] Foreign Application Priority Data

Aug. 14, 1996 [JP] Japan ................................. 8-214736

[51] Int. Cl.$^7$ ................................................... G01N 33/00
[52] U.S. Cl. ......................... 436/100; 436/101; 436/116; 436/124; 436/166; 436/169; 436/172; 422/82.06; 422/82.07
[58] Field of Search ............................. 422/82.05, 82.06, 422/82.07, 82.09, 82.11, 83, 86, 87; 436/100–102, 113, 116, 117, 118, 119–122, 127, 129, 133, 134, 166, 169, 172

[56] References Cited

U.S. PATENT DOCUMENTS

| | | | |
|---|---|---|---|
| 5,030,420 | 7/1991 | Bacon et al. | 422/82.07 |
| 5,102,625 | 4/1992 | Milo | 422/82.07 |

FOREIGN PATENT DOCUMENTS

| | | |
|---|---|---|
| 0 733 901 | 9/1996 | European Pat. Off. . |
| 1-242630 | 9/1989 | Japan . |
| 4-74964 | 3/1992 | Japan . |
| 505456 | 8/1993 | Japan . |
| 505871 | 8/1993 | Japan . |
| 243973 | 9/1995 | Japan . |
| 9-113450 | 5/1997 | Japan . |
| 91/07658 | 5/1991 | WIPO . |
| 91/07659 | 5/1991 | WIPO . |

OTHER PUBLICATIONS

F. Hibbert et al. J. Chem. Soc., Perkin Trans. 2 1977, 1624–1628, Dec. 1977.
C. L. Honeybourne et al. J. Phys. Chem. Solids 1998, 49, 1003–1008, Sep. 1988.
S. Chen et al. Chem. Abstr. 1992, 116, 224516z, Jun. 1992.
G. Hariprasad et al. J. Chem. Soc., Dalton Trans. 1996, 3429–3436, Dec. 1977.
M.J. Sienko et al. "Chemical Principles and Properties" 1974, McGraw–Hill, Inc., New York, pp. 300, 301, 321–327, & 382–383.
Y. Liu et al. *Solid State Commun.* 1996, 99, 167–171.
G. Heinzmann Wiss. Ber.–Forschungszent. Karlsruhe 1996, FZKA 5761.
C.L. Honeybourne et al. *J. Chem. Soc. Faraday Trans I.* 1984, 80, 851–863.
M.K. Freeman et al. *Anal. Chim. Acta* 1990, 241, 119–125.
M.G. Baron et al. *Sens. Actuators B* 1993, B11, 195–199.

(List continued on next page.)

*Primary Examiner*—Arlen Soderquist
*Attorney, Agent, or Firm*—Pillsbury Madison & Sutro

[57] ABSTRACT

This invention provides a method for determining the concentration of a gas to be detected by a gas detector using a gas reactive pigment, wherein the dynamic range of the detectable concentration can be controlled. The method comprising bringing a gas to be detected such as a halogen gas, a hydrogen halide gas or the like into contact with a gas detector placed in a detection area and comprising a gas reactive pigment tetraphenylporphyrin or a derivative thereof represented by the general formula (1) or a metal complex of tetraphenylporphyrin or a derivative thereof represented by the general formula (2); and irradiating said gas detector with a detection beam and measuring a color change in said gas detector to determine the concentration of said gas to be detected, wherein the measurement is carried out in the temperature range from 40 to 80° C. of said detection area; and a detection apparatus for carrying out the said method are disclosed.

4 Claims, 11 Drawing Sheets

OTHER PUBLICATIONS

R. Bonnett et al. *J. Mater. Chem.* 1993, 3, 793–799.

A. Morales–Bahnik et al. *Sens. Actuators B* 1994, 19, 493–496.

L.M. Yates III et al. *J. Sol–Gel Sci. Technol.* 1994, 2, 745–749.

Y.C. Smith et al. *Thin Solid Films,* 1996, 284–285, 911–914.

R.B. Beswick and C.W. Pitt, Journal of Colloid and Interface Science, 1988, vol. 124 (1), pp. 146–155.

Yoshihiko Sadaoka, et al., Chemical Sensors (Proceedings of the $20^{th}$ Chemical Sensor Symposium), 1995, vol. 11 Supplement A, pp. 93–96.

Yoshihiko Sadaoka, et al., Chemistry Letters, 1995, pp. 509–510 907–908.

Yoshihiko Sadaoka, et al., $12^{th}$ International Conference on the Chemistry of the Organic Solid State, Program and Abstracts, p. 146.

Kazunari Tanaka, et al. Proceedings of the $22^{nd}$ Chemical Sensor Symposium, 1996, p. 146.

M.G. Baron, R. Narayanaswamy & S.C. Thorpe, Book of Abstracts, p. 130: $2^{nd}$ European Conference on Optical Chemical Sensors and Biosensors, Apr. 19–21, 1994.

M.G. Baron, et al., Sensors and Actuators B 29, 1995, 358–362.

A. Giraudeau, et al., Inorganic Chemistry, vol. 18(1), 1979, 201–206.

A. Giraudeau, et al., J. American Chemical Soc. 101 (14), 1979, 3857–2862.

P. Bhyrappa & V. Krishnan, Inorg. Chem. 30, 1991, 239–245.

Francis D'Souza, et al., Inorg. Chem. 32, 1993, 4042–4048.

Pietro Tagliatesta, et al., Mol. Cryst. Liq. Cryst., vol. 278 (1), 1996, pp. 173–180.

Kazunari Tanaka, et al., Journal of Materials Chemistry, vol. 6 (6), 1996, pp. 953–956.

Preprint of the Joint Meeting of the ChugokuShikoku and Kyushu Branches of the Chemical Society of Japan, Oct. 21–22, 1995, Program 1F08; "Development of Photochemical Acid Gas Sensor, Porphylin—Optical Properties of Hight Molecular Complex Membranes".

Kazunari Tanaka, et al., Sixth International Meeting on Chemical Sensors, Jul. 22–25, 1996, "Optochemical HC1 Gas Detection Based on Tetraphenylporphin Dispersed".

Colin L. Honeybourne and Callum A. S. Hill, Science Department, Bristol Polytechnic, "The Chemical Degradation of Gas–Sensing Meso–Tetra–Arlyporphin Thin Films By High Levels of Dinitrogen Tetroxide".

M.G. Baron, R. Narayanaswamy, S.C. Thorpe, 1996 Elsevier Science, "Hydrophobic membrane sensors for the optical determination of hydrogen chloride gas".

GAS DETECTION METHOD AND APPARATUS USING GAS REACTIVE PIGMENT

BACKGROUND OF THE INVENTION

This application claims convention priority from Japanese patent application No. 214736/96, filed on Aug. 14, 1996, the disclosure of which is incorporated herein by reference.

This invention relates to a gas detection method using a gas detector for detecting at least one of a halogen gas, a hydrogen halide gas, an acidic gas, an oxidizing gas, a basic gas and an organic acid gas from a mixed gas containing it, and to a detection apparatus for determining the concentration of the gas.

Various methods for detecting a harmful gas in a mixed gas such as air have hitherto been proposed. It is relatively more difficult to detect a component gas in a mixed gas than to detect a component in a liquid, particularly with high accuracy over a wide gas concentration range.

There has been a strong demand for methods for rapidly and easily detecting a harmful component in a mixed gas such as air with high accuracy over a wide concentration range, particularly methods for rapidly and easily detecting a harmful component in an exhaust gas discharged from semiconductor production plants or the like, such as a halogen or a hydrogen halide with good accuracy over a wide gas concentration range.

Recently, the inventors have found that tetraphenylporphyrin and tetraphenylporphyrin derivatives or metal complexes thereof are gas reactive pigments capable of reacting with a halogen gas, a hydrogen halide gas, an acidic gas, an oxidizing gas, a basic gas or an organic acid gas (hereinafter sometimes simply referred to as a halogen gas, a hydrogen halide gas or the like). Thus, an attempt was made to provide a method for determining the concentration of a halogen gas, a hydrogen halide gas or the like using such a gas reactive pigment based on a linear calibration curve drawn from the relation between the concentration of the gas and a color spectrum change in the gas reactive pigment in contact with the gas. (J. Mater. Chem., 1996, 6(6)953–956)

However, it was found to be difficult to draw a calibration curve with sufficiently high accuracy over a wide gas concentration range to determine the concentration of a gas such as a halogen gas, a hydrogen halide gas or the like from a change in the height of peaks of the color spectrum of a pigment, e.g., tetraphenylporphyrin in contact with said gas. This is because the height of spectrum peaks increasing with an increase in gas concentration reaches a plateau while the peaks are still low, and the calibration curve provides a linearity between gas concentration and the spectrum height over a limited range. Thus, a calibration curve prepared between the concentration of a gas of interest and the height of color spectrum peaks is not useful for determining the concentration of the gas to be measured because the calibration curve covers only a limited range.

To avoid the above problem, the concentration of a gas of interest such as a halogen gas, a hydrogen halide gas or the like had to be diluted or concentrated to adjust it to a level to which a calibration curve could be applied. However, it was difficult to precisely adjust the concentration of a gas, still more difficult to include such a process of adjustment in a continuous measurement for gas concentration.

In order to broaden the gas concentration range measurable in a method for determining the concentration of a gas such as a halogen gas using a gas detector comprising a gas reactive pigment, the inventors also made an attempt to use a plurality of gas detectors comprising different amounts of a gas reactive pigment therein. (J. Mater. Chem., 1996, 6(6)953–956; and U.S. Ser. No. 08/728,529, the disclosure of which is incorporated herein by reference) However, the use of a plurality of gas detectors in the attempt was inconvenient.

SUMMARY OF THE INVENTION

An object of the invention is to eliminate the above drawbacks of the prior art and to provide a detection method and a detection apparatus with i) a wide measurable range (i.e. dynamic range), ii) a quick response and iii) a wide linear relationship between the concentration of a gas to be detected and the height of color spectrum peaks.

Another object of the invention is to provide a detection method and a detection apparatus which can detect a gas to be detected not only in a wide concentration range but also with high sensitivity.

The inventors previously developed a gas detector which provides higher spectrum peaks (improved sensitivity) until its light absorbing ability is saturated or reaches a plateau in response to the increase of gas concentration. The detector was developed in search of substances capable of improving the sensitivity of gas reactive pigments and amounts thereof to be included in the gas detector. Following efforts of the inventors to develop a method for detecting a gas such as a halogen gas using said gas detector, the following fact has been revealed.

Namely, the inventors have found that the threshold gas concentration which plateaus the color spectrum peaks of the gas detector varies depending on the temperature of a gas detector through which a detection beam is transmitted or from which a detection beam is reflected. That is to say, the sensitivity of the gas detector is greatly influenced by the temperature of the detection area of the gas detector exposed to the gas to be detected under irradiation of the detection beam. This invention has been accomplished based on said finding.

Numeral references indicate the following members, respectively:

| 1 Measuring cell | 2 Substrate |
|---|---|
| 3 Detector | 4 Sample gas |
| 5 Exhaust gas | 6 Halogen lamp |
| 7 Projector/receptor | |
| 8 Optical fiber | 9 Heater |
| 10 Outer temperature controller | |
| 11 Multiphotometric detector | |
| 12 Computer | 13 Gas passage |
| 14 Projector | 15 Receptor. |

DESCRIPTION OF THE PREFERRED EMBODIMENTS

Accordingly, this invention provides a gas detection method using a gas reactive pigment, which comprises
  providing a gas detector comprising, as the gas reactive pigment, a tetraphenylporphyrin represented by the following general formula (1) or a derivative thereof, or a metal complex of tetraphenylporphyrin represented by the following general formula (2) or a derivative thereof;
  bringing at least one gas to be detected which is selected from the group consisting of a halogen gas, a hydrogen halide gas, an acidic gas, an oxidizing gas, a basic gas and an organic acid gas into contact with said gas detector;
  maintaining the temperature of the detector or the vicinity thereof in the range from 40 to 90° C., preferably from 40 to 80° C., and more preferably from 40 to 60° C. while said detector is in contact with the gas to be detected;
  irradiating the detector with a light beam while said detector is in contact with the gas to be detected and said temperature is maintained; and
  measuring the spectrum of the light which is reflected or transmitted from said gas detector, whereby the intensity of the spectrum is an indication of the concentration of said gas to be detected:

Formula (1)

Formula (2)

wherein in formula (1) and (2),

R represents a substituent selected from the group consisting of a hydrogen atom, a halogen atom, a nitro group, a cyano group and an alkoxy group preferably having 1–10 carbon atoms, G represents a substituent on the four phenyl groups selected from the group consisting of a halogen atom, a hydroxyl group, a sulfonic acid group, a carboxyl group, an alkyl group preferably having 1–10 carbon atoms, an alkoxy group preferably having 1–10 carbon atoms and an amine group, a, b, c and d may be the same or different and each represents an integer of 0 to 5, and the substitution position of G on each phenyl group may also be the same or different, M represents a transition metal.

Detection temperature

In accordance with the gas detection method of this invention, the temperature of the detector comprising the gas reactive pigment is maintained at 40° C. or higher while said detector is in contact with the gas to be detected. This is important to detect a gas not only in a wide gas concentration range but also with a high response speed. The inventors have found that the higher the temperature the wider the measurable concentration range of the gas to be detected. It is therefore preferred that the detection is conducted at a temperature as high as possible when a broader measurement range is desired, and the upper limit of the temperature, for example, 80 or 90° C. will be determined by practical reasons such as stability of the gas reactive pigments, the corrosive action of the gas to be detected and the like. In any event, a skilled person will understand that the temperature may be selected in the range from 40 to 90° C. depending on the purpose and situation.

Further, the measurable concentration range of a gas to be detected by the gas detector comprising the pigment can be controlled by appropriately selecting the temperature of the detection area in the range from 40 to 80° C. Thus, "the measurable concentration range of a gas to be detected can be controlled" by selecting the dynamic range of the gas detector so that (1) the concentration of a gas to be detected can be determined by using said gas detector with a higher accuracy but in a narrower concentration range or (2) the concentration of a gas to be detected can be determined by using said gas detector over a wider concentration range but with a less accuracy. More specifically, the gas detector may be brought into contact with a gas to be detected with varying concentrations at several different temperatures in the range from 40 to 80° C. to draw several calibration curves representing the relation between the color density (spectrum) of the gas detector and the concentration of the gas to be detected. Whereby, it is possible to improve the sensitivity of the detection by employing a calibration curve wherein the spectrum changes rapidly in response to the varying gas concentrations. On the other hand, by using a calibration curve which is linear over a wider gas concentration range, detection of the gas over a wider concentration range will be possible.

Gas Reactive Pigment

The tetraphenylporphyrin represented by the general formula(1) or a derivative thereof, and the metal complex of tetraphenylporphyrin represented by the general formula (2) or a derivative thereof are generally known and described, for example, in Inorg. Chem. (1991), 30, 239–245, the disclosure of which is incorporated herein by reference.

With reference to the general formula (1) representing the structure of a gas reactive pigment used in the gas detector of this invention, each substituent R on four pyrrole rings belonging to the porphyrin nucleus in the general formula (1) represents a hydrogen atom, a halogen atom, a nitro group, a cyano group or an alkoxy group, and the numbers a, b, c and d of the substituents $(G)_a$, $(G)_b$, $(G)_c$ and $(G)_d$ on the four phenyl groups attached to the porphyrin nucleus may be the same or different and represent an integer of 0 to 5. The position of these substituents on the four phenyl groups may also be the same or different. G represents a substituent selected from a hydrogen atom, a halogen atom, a hydroxyl group, a sulfonic acid group, a carboxyl group, an alkyl group, an alkoxy group and an amine group.

When the both of R and G represent a hydrogen atom, the gasreactive pigment is tetraphenylporphyrin.

With reference to the general formula (2) representing the structure of a gas reactive pigment used in the gas detector of this invention, each substituent R on four pyrrole rings belonging to the porphyrin nucleus in the general formula (2) represents a hydrogen, a halogen atom, a nitro group, a cyano group or an alkoxy group. M represents a transition metal atom such as zinc, copper, iron, nickel, cobalt, manganese, titanium, aluminium, etc., among which zinc, cobalt and iron are especially preferred. Here, the halogen atom means F, Cl, Br, I and At. G and a, b, c and d have the same meanings as defined for the general formula (1).

As examples of the tetraphenylporphyrin of the formula (1) or a derivative thereof
tetraphenylporphyrin;
tetrakis(4-bromophenyl)porphyrin;
tetrakis(4-chlorophenyl)porphyrin;
tetrakis(4-metoxyphenyl)porphyrin;
tetrakis(4-octoxyphenyl)porphyrin;
5-hydroxyphenyl-10,15,20triphenylporphyrin;
tetrabromotetraphenylporphyrin; and
octabromotetraphenylporphyrin are mentioned.

As an example of the metal complex of tetraphenylporphyrin of the formula (2) or a derivative thereof zinc tetrabromotetraphenylporphyrin is mentioned.

The gas reactive pigment reacts with a gas such as a halogen gas, a hydrogen halide gas, an acidic gas, an oxidizing gas, a basic gas or an organic acid gas (gas to be detected) to cause a change in the electronic state of the pigment molecules. Said change in the electronic state gives rise to a change in color or absorption spectrum of the pigment. Thus, it is possible to prepare a gas detector comprising the gas reactive pigment, and then a gas to be detected is brought into contact with the gas detector, while the detector is being irradiated with a detection beam, to measure a color change in the reactive pigment supported on the carrier of the gas detector by way of the spectrum change in the detection beam transmitted through or reflected from said gas detector. This mode of measurement will be hereinafter simply referred to as measurement of a spectrum change in the gas reactive pigment.

In this way, a change of color or a change of color density of the gas detector comprising the gas reactive pigment in contact with a gas can be measured as a change of the position and/or height of peaks of the spectrum of the reactive pigment. In this invention, the source of the detection beam directed to the gas detector to measure a change in the reactive pigment as a change in the spectrum of the beam transmitted through or reflected from the gas detector may be natural white light, halogen lamp light or one or more monochromatic beams.

The "original color" of the gas reactive pigment, i.e. the position and/or height of peaks of the spectrum of the pigment before contact with said gas and a "reaction-induced color change", i.e. a change of the position and/or height of peaks of the spectrum of the pigment in contact with said gas depend on the individual gas reactive pigment.

The change in the position and/or height of spectrum peaks of the gas reactive pigment in response to the gas to be detected does vary depending on the pigment and the species of the gas to be detected, but the said change is reversible, and therefore, in the absence of the gas to be detected, the spectrum of the pigment is restored quickly so that the pigment is ready for the next round of continuous measurement.

In determining the concentration of a gas of interest in a sample by measuring the color density of a gas detector, the reproducibility of measurements is a very important factor. Measurements with good reproducibility may typically be obtained by observing a change in the optical density of detection beams with varying wavelengths directed to the sample, i.e. by scanning the spectra of the detection beam transmitted through or reflected from the gas detector to find out peaks of the spectra and then using a beam of a wavelength showing the peak value as a detection beam to measure the color density of the material of interest.

Gas Detector

A gas reactive pigment is normally applied on a carrier to increase the area in which the pigment comes into contact with a gas. Therefore, the term "gas detector" herein collectively means not only gas reactive pigments themselves but also those supported on a carrier.

The gas detector may be prepared by dissolving one of the above mentioned gas reactive pigments in a solvent together with a matrix polymer and a plasticizer for said polymer, applying said solution on an appropriate carrier and drying it. Preferred solvents are those which are capable of dissolving both polymers and pigments, such as dimethylformamide, dioxane, toluene and a mixture of toluene and ethanol (8:2). It is known that the sensitivity of the gas detector varies with the concentration of the gas reactive pigment as well as the ratio between the matrix polymer and the plasticizer. These factors are selected so that the gas detector used in this invention preferably has a high sensitivity.

The matrix polymer and plasticizer used in the gas detector are not specifically limited provided that they are transparent and soluble in a solvent used for dissolving the gas reactive pigment and that they do not have any substantial absorption peak in the vicinity of the absorption wavelength of the gas reactive pigment.

Examples of such a polymer material include Nafion, ethyl cellulose, ethoxyethyl cellulose, cellulose acetate, cellulose acetate butyrate, modified starch, polyvinylpyrrolidone, vinylpyrrolidone copolymers, polymethyl vinyl ether and methyl vinyl ether copolymers.

The plasticizer mixed with said polymer material may include phthalates such as dibutyl phthalate or diethylhexyl phthalate (also called as dioctyl phthalate); glycolates such as ethyl phthalyl ethyl glycolate or butyl phthalyl ethyl glycolate; or phosphates such as tributyl phosphate or tricresyl phosphate.

Shape of the gas detector is not specifically limited so far as it comprises at least a gas reactive pigment, preferably with a matrix polymer and a plasticizer. It may be comprised of a unsupported polymer composition containing a gas reactive pigment, or may be such a composition supported on a carrier. Preferred carriers include an alumina substrate, a glass plate, an optical fiber, paper sheet, glass beads and silica gel, but may not be limited to these examples.

The method for measuring a gas to be detected using the detector is not specifically limited so far as it can detect at least one gas of a halogen gas, a hydrogen halide gas, an acidic gas, an oxidizing gas, a basic gas and an organic acid gas by bringing the gas to be detected into contact with said gas detector and measuring a color change in said gas detector.

The color change may be measured by comparing color densities of said detector by visual observation, but preferably the measurement is conducted in one of the following manners:

(1) the color change in said gas reactive pigment may be measured as a spectrum change of a light beam directed to said detector;

(2) the color change in said gas reactive pigment may be measured under irradiation of said detector with a light beam to measure a change in the absorbed amount of light as the beam transmitted through or reflected from said detector or to measure a change in the amount of fluorescence;

(3) the color change in said gas reactive pigment may be measured under irradiation of said detector with a light beam to measure a color change at a plurality of wavelengths as the beam transmitted through or reflected from said detector; or (4) the color change in said gas reactive pigment may be measured under irradiation of said detector with a light beam to measure a color change at a plurality of wavelengths as the beam transmitted through or reflected from said detector and to measure the difference in the color change at the plurality of wavelengths.

Apparatus

Figure 2:
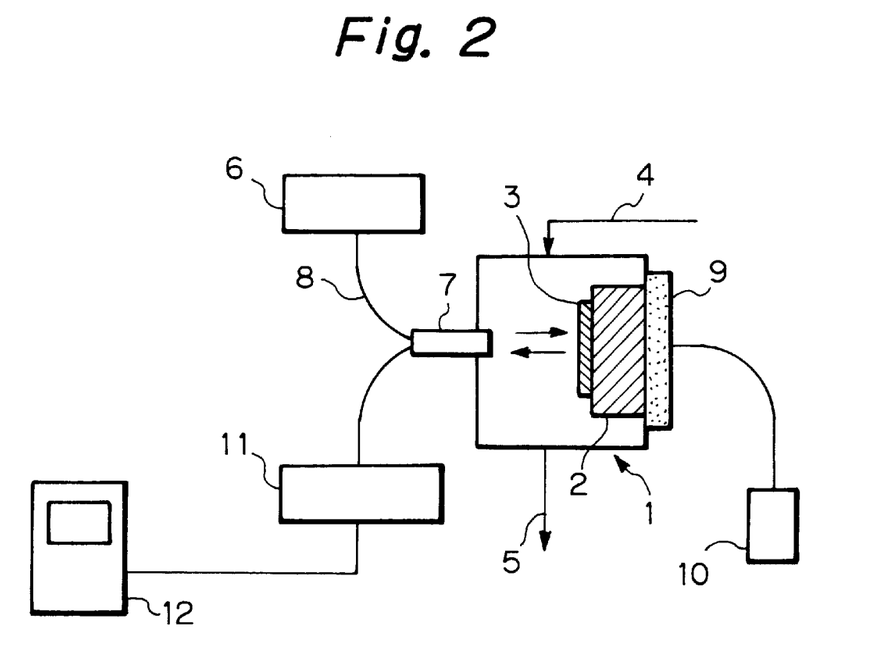
FIG. 2 is an explanatory view showing the structure of an example of a temperature-controllable gas detection apparatus according to this invention.

The structure of the detection apparatus of this invention using the gas detector is not limited to any specific structure so far as said gas detector is provided in the passage of a gas to be detected. A preferred apparatus has a structure as shown in FIG. 2. Referring to FIG. 2, a gas detector 3 is formed on a substrate 2 housed in a measuring cell 1. A heater 9 and an outer temperature controller 10 are provided to control the temperature of the gas detector 3. A projector/receptor 7 is provided in front of the substrate 2 of the gas detector 3. The projector/receptor 7 projects a beam from a halogen lamp 6 by way of an optical fiber 8 and receives the beam reflected from the substrate 2 under the gas detector 3. The signal received by the receptor is transmitted to a multiphotometic detector 11. A sample gas 4 is passed through the measuring cell 1, while the inside of the cell 1 is maintained at a temperature within the range of 40 to 80° C., to measure a change in the reflective spectrum after the reaction with TPP in the gas detector 3. The results of the measurement are then introduced to a computer 12 and the information is processed therein.

Figure 3:
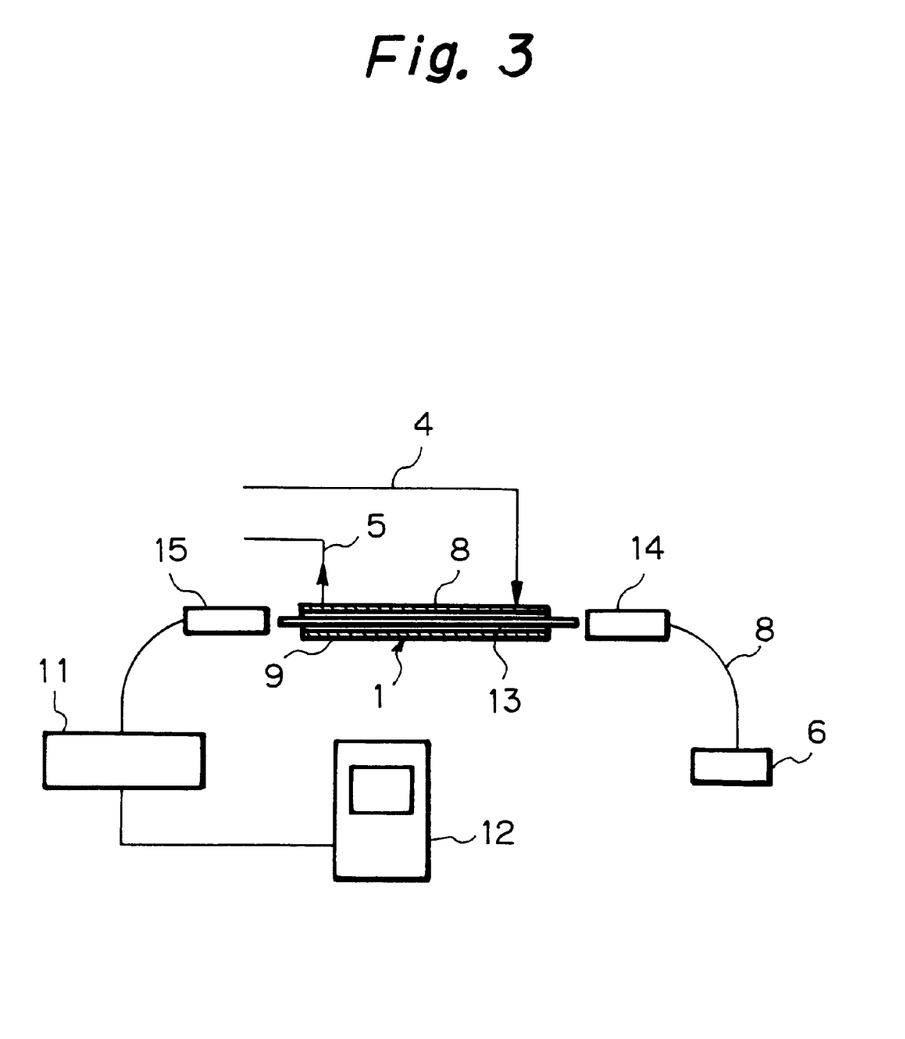
FIG. 3 is an explanatory view showing the structure of another example of a temperature-controllable gas detection apparatus according to this invention.

Another example of the detection apparatus is shown in FIG. 3, wherein a gas detector is comprised of an optical fiber 8 coated with the above-mentioned solution containing a gas reactive pigment. The gas detector is provided in a gas passage 13 through which a sample gas is passed. A detection beam from a halogen lamp 6 is introduced into the optical fiber 8 via a projector 14 and the beam leaving the optical fiber 8 is received by a receptor 15 and the signal is transmitted to a multiphotometric detector 11. The projector and the receptor may be combined in one unit.

Figure 1:
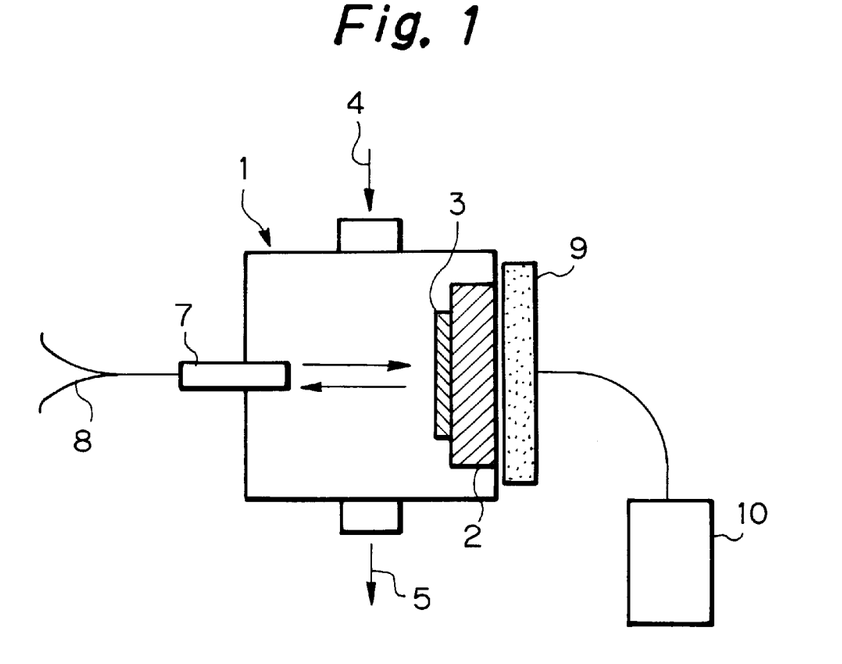
FIG. 1 is an explanatory view showing the structure in section of an example of a measuring cell used in this invention.

FIG. 1 shows details of the measuring cell used in the embodiment of the apparatus of FIG. 2. The measuring cell 1 includes an inlet tube and an outlet tube for allowing a sample gas to pass through, a detector 3 on a substrate therefor 2, a temperature-controlling unit including a heater 9 and a temperature controller 10, and an orifice to allow the entrance and exit of a detection beam or the like. The area of the measuring cell 1 is the detection area.

In the detection area of the detection apparatus shown in FIG. 2, the gas detector 3 with the alumina substrate 2 is placed in the measuring cell 1. The measuring cell 1 is equipped with the heater 9 whose temperature is controlled by the outer temperature controller 10 as shown in FIG. 1. Said gas detector 3 is brought into contact with a sample gas introduced via a gas inlet. The detector is then irradiated with a beam which is guided through an optical fiber from the projector/receptor 7 while the measuring cell 1 is maintained at a preset temperature by heating the associated heater 9 by the outer temperature controller 10. The beam reflected from the gas detector 3 is received by the projector/receptor 7 and then measured by the multiphotometric detector 11 through the optical fiber 8. The sample gas in the measuring cell 1 is discharged as exhaust gas from a gas outlet.

EXAMPLE

A gas detection method of this invention using the above-mentioned gas detection apparatus will now be explained more in detail by way of examples, but the following example should not be construed as limiting this invention. Although the invention will be explained in the following examples with reference to the detection apparatus of FIG. 2, similar results will be achieved by a detection apparatus of different types such as that shown in FIG. 3. It will be appreciated that the invention can be practiced in modified forms without departing from the scope and the spirit of the invention.

Example 1

A gas detector was prepared from tetraphenylporphyrin (TPP), ethyl cellulose (EC) as a matrix polymer and diethylhexyl phthalate as a plasticizer by adding diethylhexyl phthalate in an amount of 0.33 g per 1 g of ethyl cellulose and then adding $1.0 \times 10^{-5}$ moles of tetraphenylporphyrin to thus plasticized matrix, and the gas detector was applied on an alumina substrate.

The gas detector was placed in a measuring cell equipped with means for maintaining the inside of the cell at a desired temperature. Gas mixtures containing hydrogen chloride at 0, 1, 2, 5, 10, 15, 20, 30, 40 and 50 ppm in nitrogen were sequentially introduced into the measuring cell set at a temperature of 30° C., 45° C. or 60° C. so that the gas mixtures containing hydrogen chloride would come into contact with the gas detector. Measurements were taken with a detection beam at 450 nm and the results of the beam reflected from the gas detector are shown in FIGS. 4 and 5 as measured by a multiphotometric detector.

Figure 4:
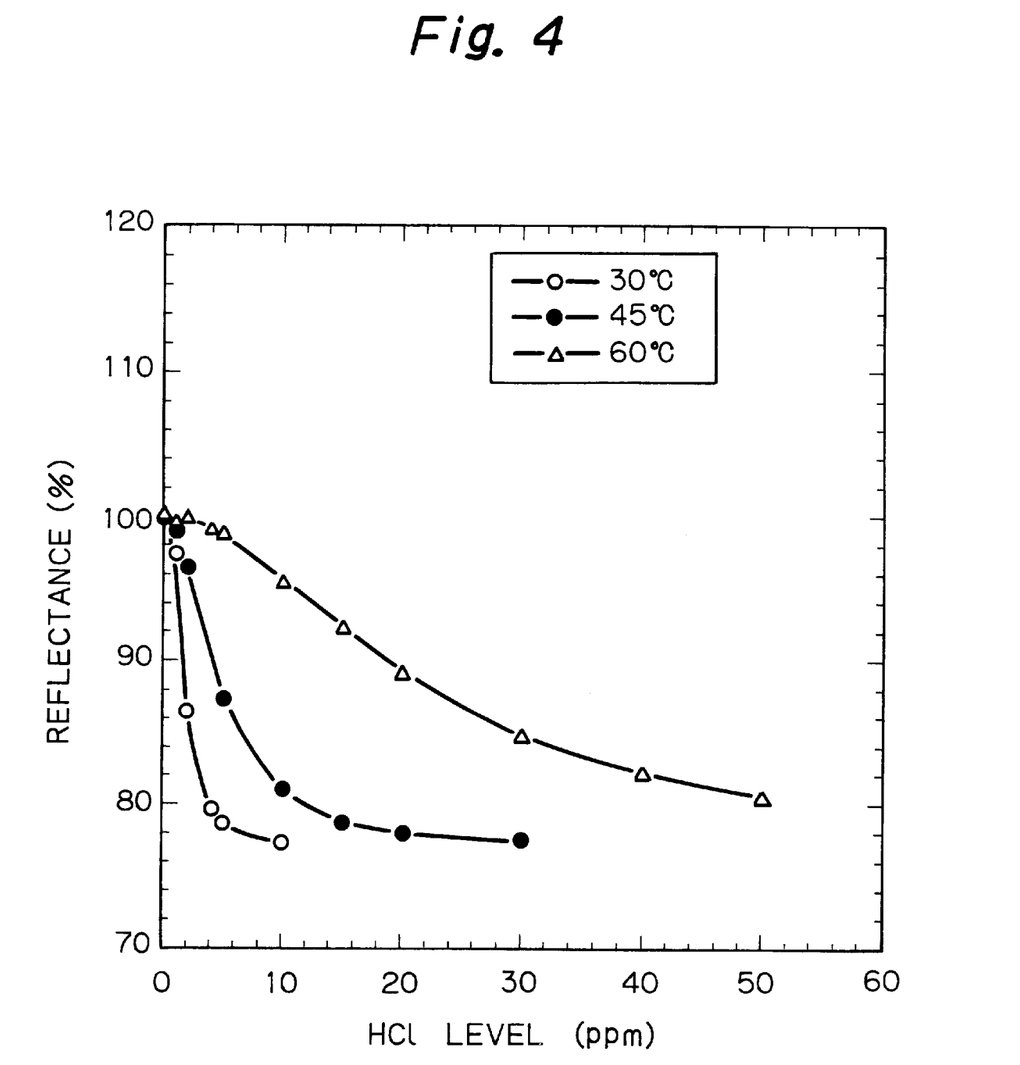
FIG. 4 is a graph showing the relation between hydrogen chloride concentration and the reflectance of a detection beam at three temperature levels when a gas detector comprising tetraphenylporphylin (TPP) reacts with a nitrogen gas containing hydrogen chloride (measured at 450 nm).

FIG. 4 shows the effect of temperature on the concentration range of HCl measurable by the detector comprising TPP. The height of the absorption peak at 450 nm was plotted against HCl concentration at each temperature. The figure shows that the concentration of hydrogen chloride gas could be measured only within the range from 0 ppm to 10 ppm by the prior measurement using a measuring cell set at a temperature of 30° C. while the concentration of hydrogen chloride gas in the range from 0 ppm to 30 ppm could be measured by raising the temperature of the measuring cell to 45° C. and even the concentration of hydrogen chloride gas in the range from 0 ppm to 50 ppm could be measured by raising the temperature of the measuring cell to 60° C.

Figure 5:
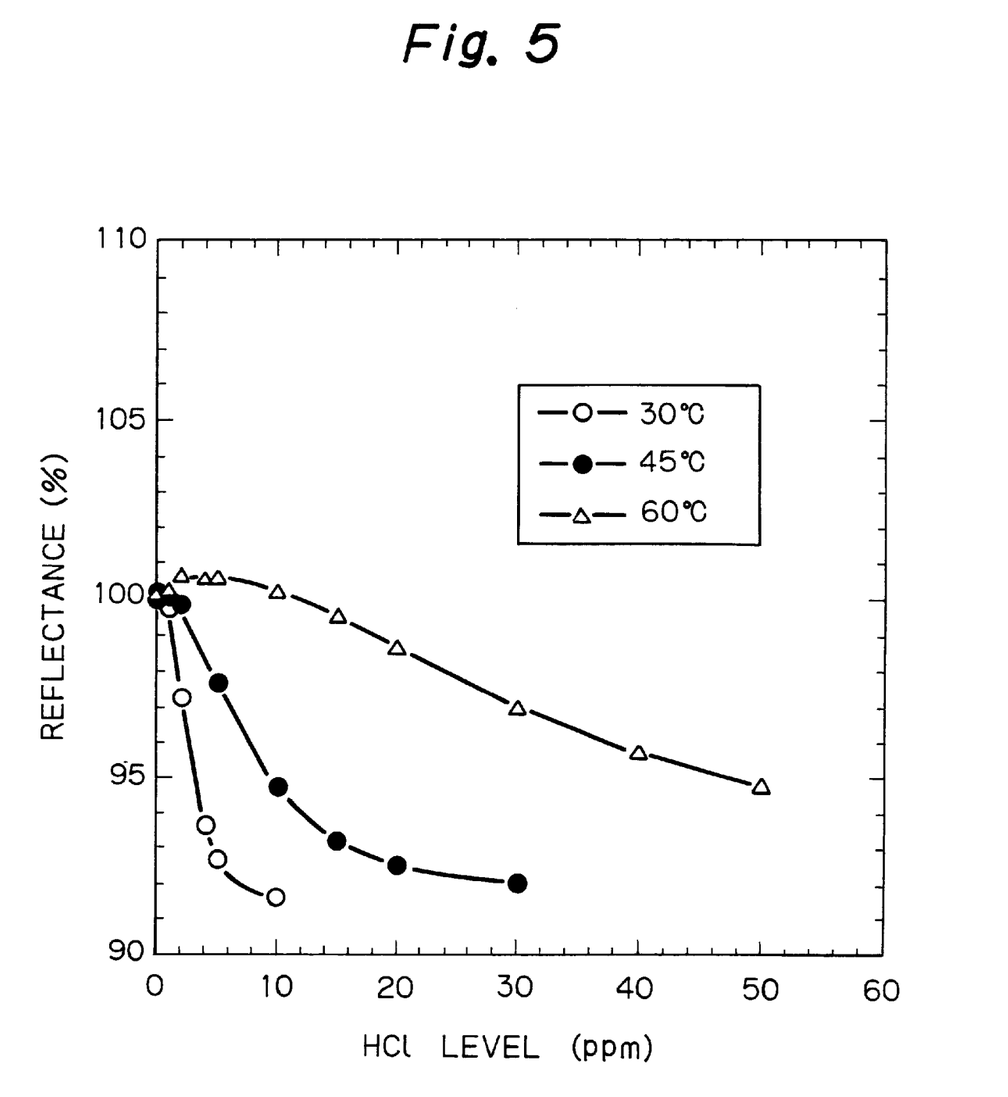
FIG. 5 is a similar graph as in FIG. 4, but the measurement was conducted at 660 nm.

FIG. 5 shows a similar graph as in FIG. 4, but the measurement was conducted at 660 nm.

Figure 6:
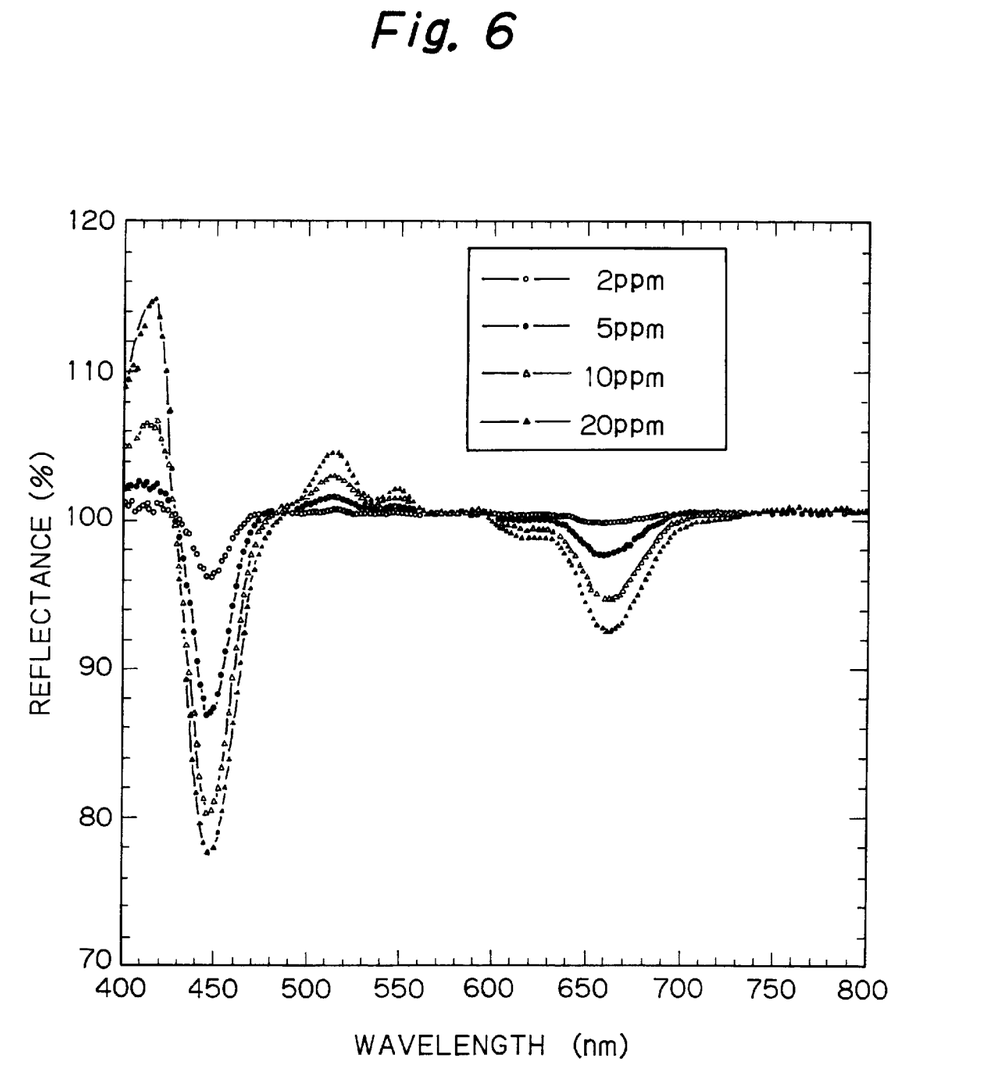
FIG. 6 is a graph showing spectrum patterns of TPP formed at 45° C. in response to the indicated HCl concentrations.

FIG. 6 shows various spectrum patterns of TPP formed at 45° C. in response to the indicated HCl concentrations.

Example 2

A similar test as in Example 1 was conducted using 5,10,15,20-tetrakis(4-bromophenyl)-21H,23H-porphyrin (TP(4-Br)P) as the pigment. $1.18 \times 10^{-5}$ moles of the pigment and $2.56 \times 10^{-3}$ moles of the plasticizer were used per 1 g of ethyl cellulose. The results are summarized in FIGS. 7 and 8.

Figure 7:
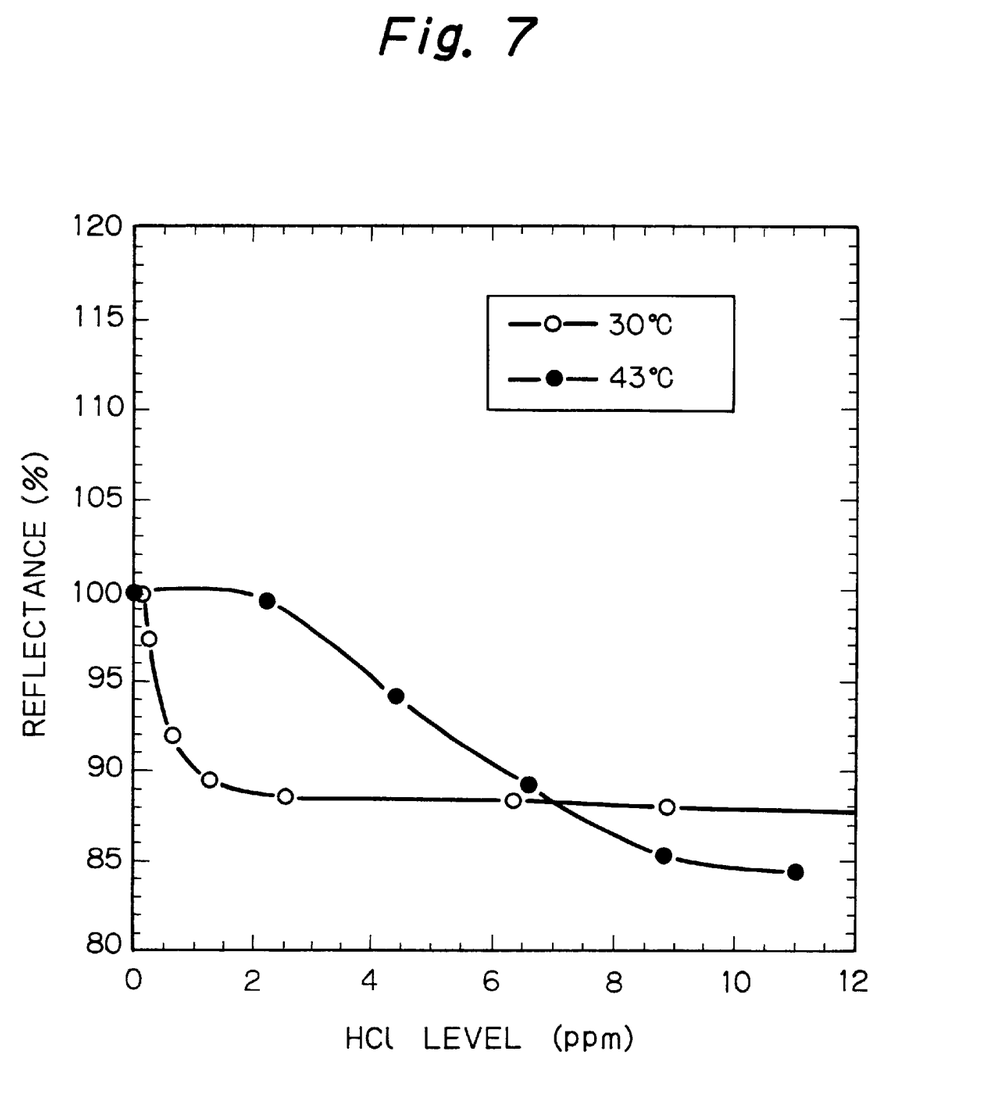
FIG. 7 is a graph showing the relation between hydrogen chloride concentration and the reflectance of a detection beam at two temperature levels when a gas detector comprising 5,10,15,20-tetrakis(4-bromophenyl)-21H,23H-porphyrin (TP(4-Br)P) reacts with a nitrogen gas containing hydrogen chloride (measured at 452 nm).
Figure 8:
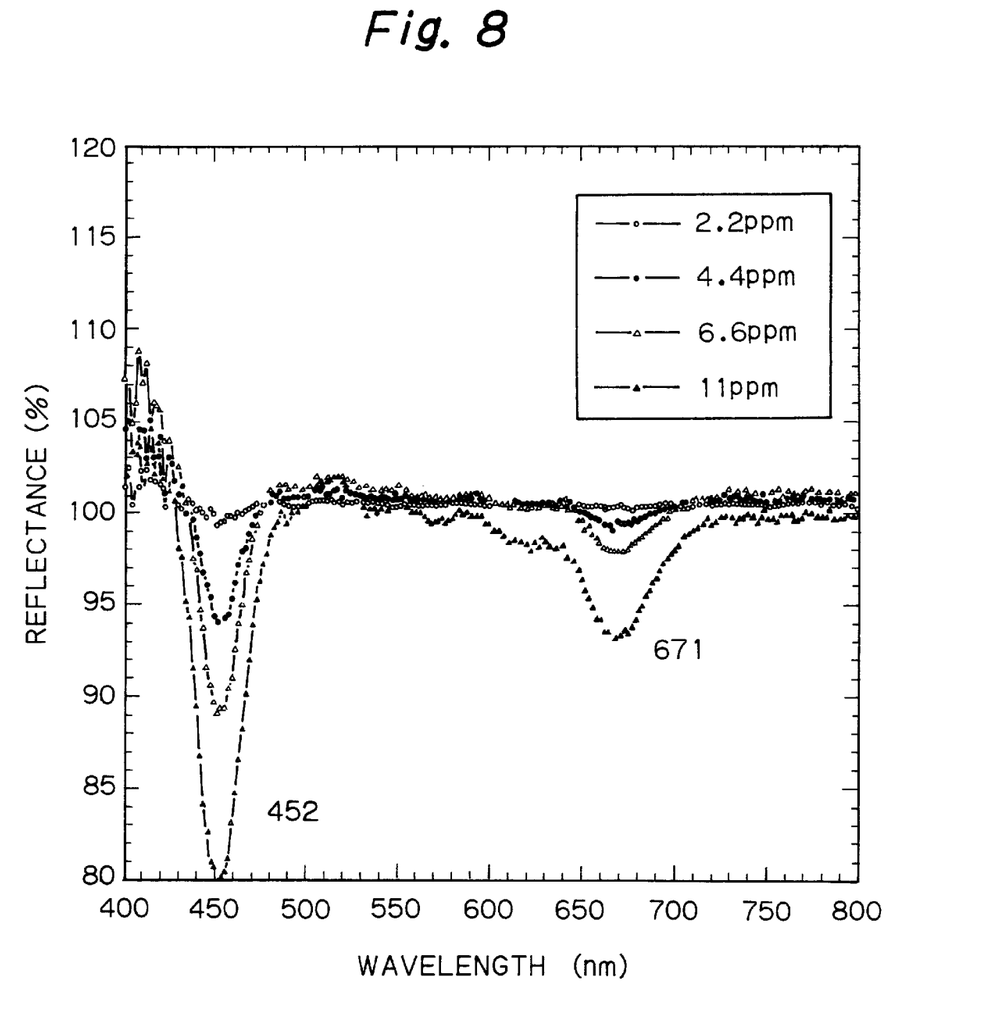
FIG. 8 is a graph showing spectrum patterns of (TP(4-Br)P) formed at 45° C. in response to the indicated HCl concentrations.

FIG. 7 shows the effect of temperature on the concentration range of HCl measurable by the detector comprising TP(4-Br)P. The height of the absorption peak at 452 nm was plotted against HCl concentration at each temperature. FIG. 8 shows various spectrum patterns of TP(4-Br)P formed at 43° C. in response to the indicated HCl concentrations.

Example 3

A similar test as in Example 1 was conducted using tetrabromotetraphenylporphyrin (Br4 TPP) as the pigment. $1.10 \times 10^{-5}$ moles of the pigment and $2.56 \times 10^{-3}$ moles of the plasticizer were used per 1 g of ethyl cellulose. The results are summarized in FIGS. 9 and 10.

Figure 9:
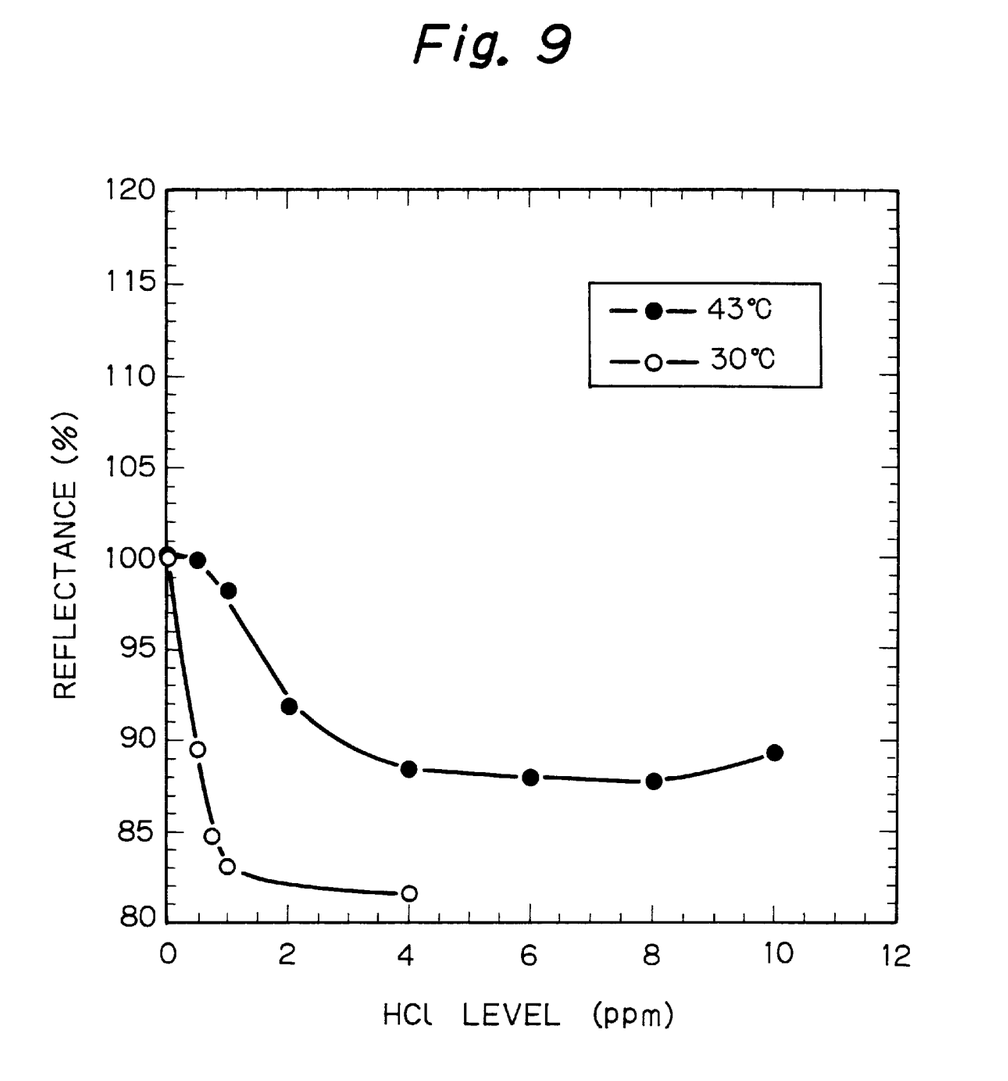
FIG. 9 is a graph showing the relation between hydrogen chloride concentration and the reflectance of a detection beam at two temperature levels when a gas detector comprising tetrabromotetraphenylporphyrin (Br4 TPP) reacts with a nitrogen gas containing hydrogen chloride (measured at 452 nm).
Figure 10:
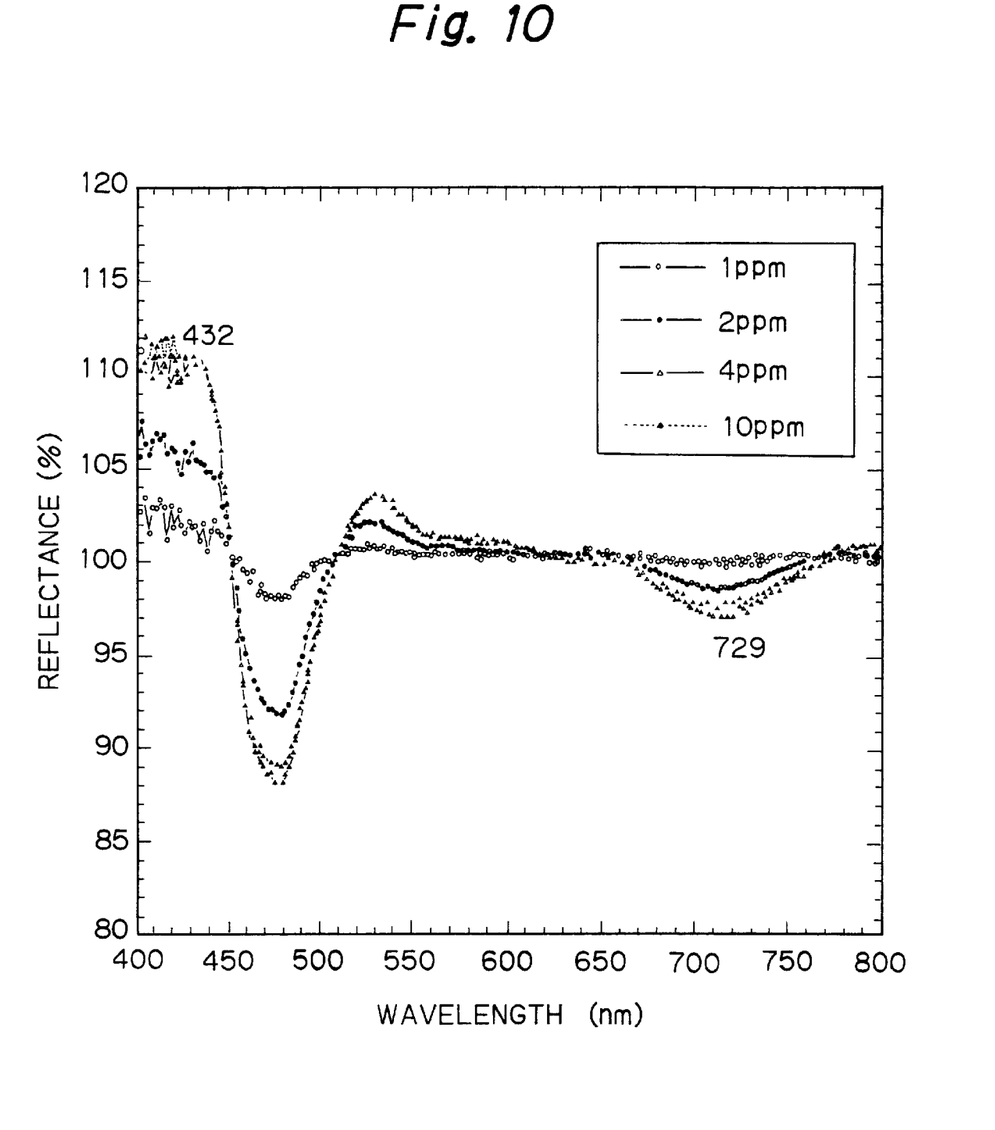
FIG. 10 is a graph showing spectrum patterns of Br4 TPP formed at 45° C. in response to the indicated HCl concentrations.

FIG. 9 shows the effect of temperature on the concentration range of HCl measurable by the detector comprising Br4 TPP. The height of the absorption peak at 452 nm was plotted against HCl concentration at each temperature. FIG. 10 shows various spectrum patterns of Br4 TPP formed at 43° C. in response to the indicated HCl concentrations.

Example 4

A similar test as in Example 1 was conducted using zinc tetrabromotetraphenylporphyrin (Zn Br4 TPP) as the pigment. $1.10 \times 10^{-5}$ moles of the pigment and $2.56 \times 10^{-3}$ moles of the plasticizer were used per 1 g of ethyl cellulose. The results are shown in FIGS. 11 and 12.

Figure 11:
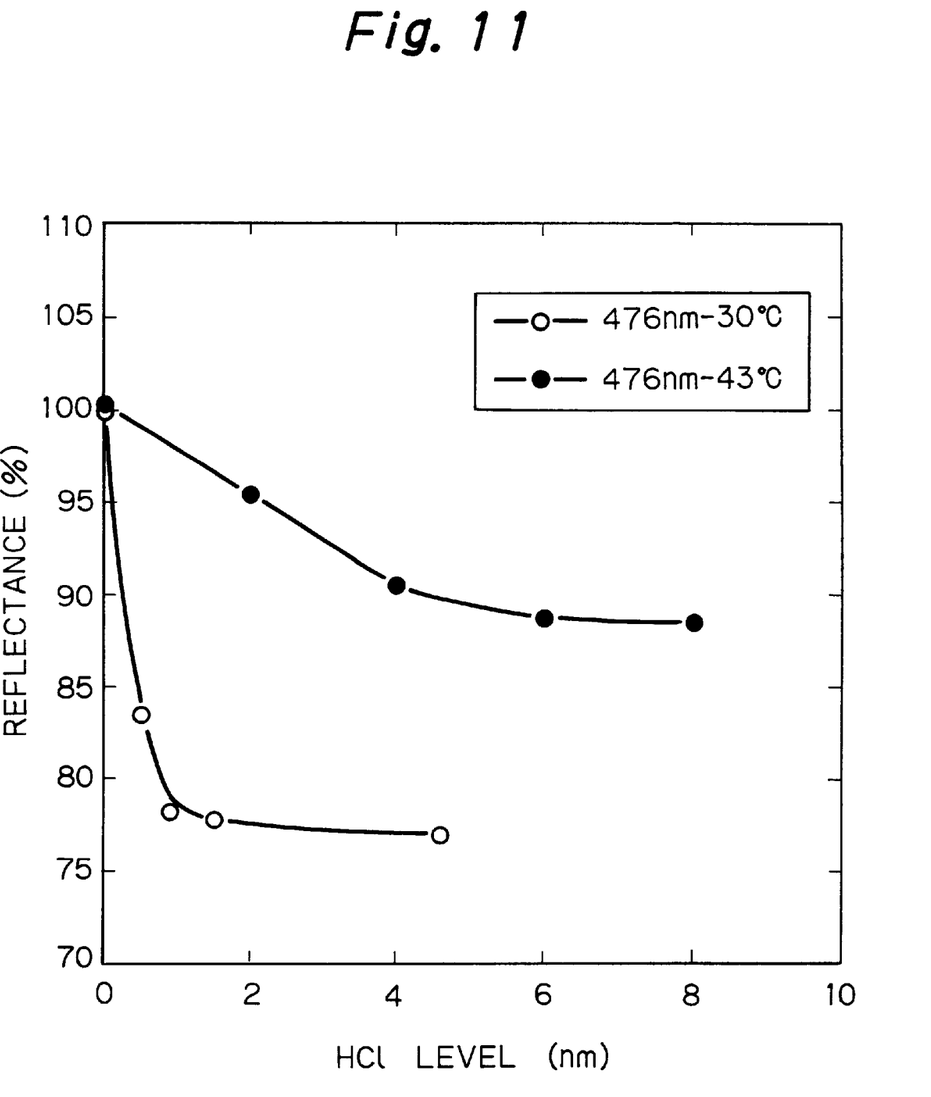
FIG. 11 is a graph showing the relation between hydrogen chloride concentration and the reflectance of a detection beam at two temperature levels when a gas detector comprising zinc tetrabromotetraphenylporphyrin (Zn Br4 TPP) reacts with a nitrogen gas containing hydrogen chloride (measured at 476 nm).
Figure 12:
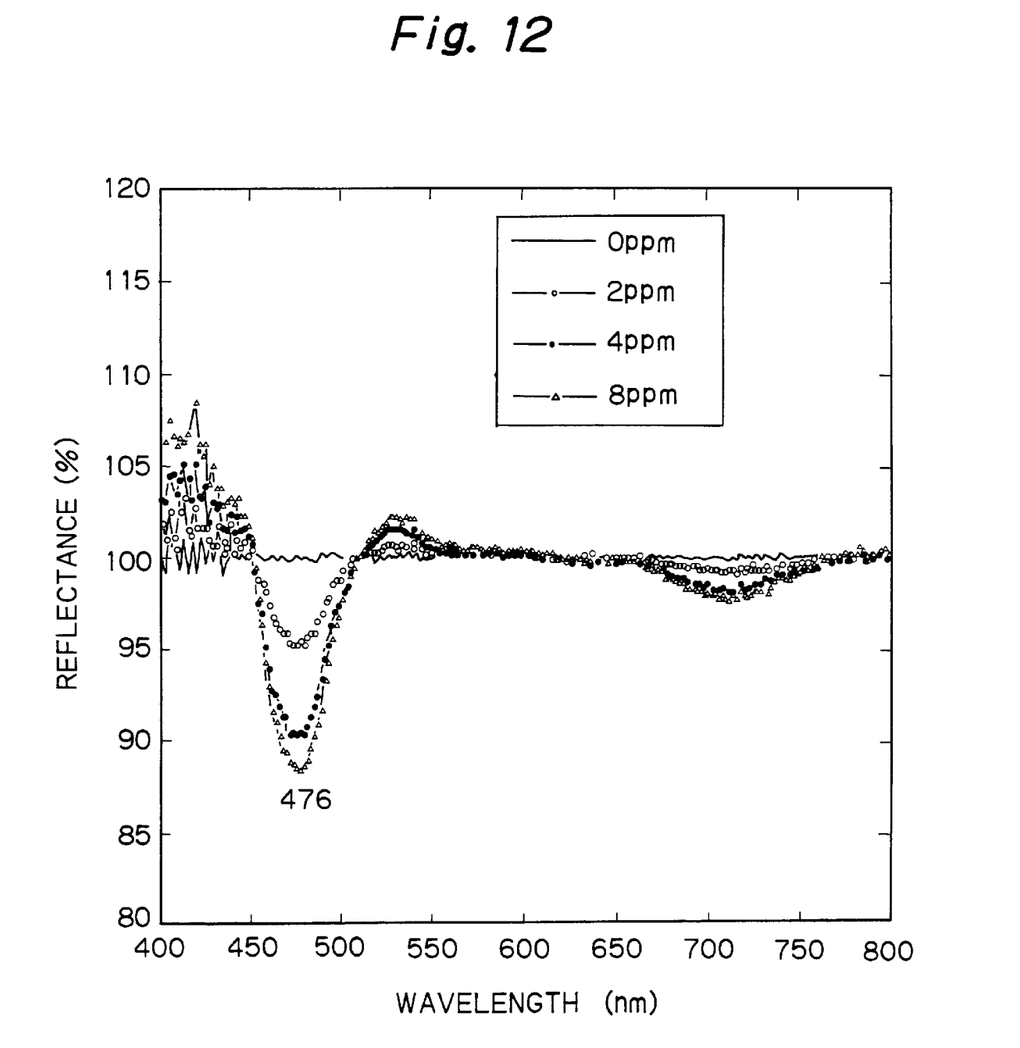
FIG. 12 is a graph showing spectrum patterns of Zn Br4 TPP formed at 45° C. in response to the indicated HCl concentrations.

FIG. 11 shows the effect of temperature on the concentration range of HCl measurable by the detector comprising Zn Br4 TPP. The height of the absorption peak at 476 nm was plotted against HCl concentration at each temperature. FIG. 12 shows various spectrum patterns of Zn Br4 TPP formed at 43° C. in response to the indicated HCl concentrations.

In a gas detection method and apparatus for detecting a gas to be detected by bringing the gas to be detected into contact with a gas detector comprising a gas reactive pigment tetraphenylporphyrin or a tetraphenylporphyrin derivative or a metal complex thereof, the detectable concentration range of the gas can be broadened and the detection speed, or response speed, can be improved by raising the temperature of the gas detection area to a range from 40 to 80° C.

What is claimed is:

1. A gas detection method using a gas reactive pigment, which comprises, providing a gas detector comprising, as the gas reactive pigment, a tetra phenylporphyrin represented by the following general formula (1), or a metal complex of tetraphenylporphyrin represented by the following general formula (2);

bringing at least one gas to be detected which is a hydrogen halide gas, into contact with said gas detector;

maintaining the temperature of the detector or the vicinity thereof in the range from 40 to 80° C. while said detector is in contact with the gas to be detected whereby said temperature provides the method with a broader measurable concentration range of the gas to be detected than the measurable concentration range provided by a temperature below 40° C.;

irradiating the detector with a light beam while said detector is in contact with the gas to be detected and said temperature is maintained; and measuring the spectrum of the light which is reflected or transmitted from said gas detector, whereby the intensity of the spectrum is an indication of the concentration of said gas to be detected:

Formula (1)

Formula (2)

wherein in formula (1) and (2),

R represents a substituent selected from the group consisting of a hydrogen atom and a halogen atom, G represents a substituent on the four phenyl groups selected from the group consisting of a halogen atom, a, b, c and d may be the same or different and each represents an integer of 0 to 5, and the substitution position of G on each phenyl group may also be the same or different, M represents a transition metal which is Zn.

2. A gas detection method according to claim 1, wherein said gas detector comprises the gas reactive pigment supported on a carrier together with a matrix polymer and a plasticizer.

3. A gas detection method according to claim 1, wherein the gas reactive pigment is tetraphenylporphyrin and the measurement of the spectrum is conducted at an approximate wavelength of 450 nm or 660 nm.

4. A gas detection method according to claim 1, wherein HCl contained at a concentration from 0 to 50 ppm in a mixed gas is detectable without need of previous dilution or concentration of the mixed gas.

* * * * *